United States Patent
Fan et al.

(10) Patent No.: US 7,985,867 B2
(45) Date of Patent: Jul. 26, 2011

(54) PROCESS FOR PRODUCING EPOXIDES

(75) Inventors: William W. Fan, Lake Jackson, TX (US); Christian D. Kneupper, Brazoria, TX (US); Sascha Noormann, Gruenendeich (DE); Renate Patrascu, Stade (DE)

(73) Assignee: Dow Global Technologies LLC (US)

( * ) Notice: Subject to any disclaimer, the term of this patent is extended or adjusted under 35 U.S.C. 154(b) by 0 days.

(21) Appl. No.: 12/508,465

(22) Filed: Jul. 23, 2009

(65) Prior Publication Data

US 2010/0029959 A1 Feb. 4, 2010

Related U.S. Application Data

(60) Provisional application No. 61/085,758, filed on Aug. 1, 2008.

(51) Int. Cl.
C07D 301/24 (2006.01)
B01D 3/34 (2006.01)

(52) U.S. Cl. ............. 549/520; 549/521; 203/37; 203/38

(58) Field of Classification Search .................. 549/520, 549/521; 203/37, 38
See application file for complete search history.

(56) References Cited

U.S. PATENT DOCUMENTS

| 4,634,784 A | 1/1987 | Nagato et al. |
| 5,532,389 A | 7/1996 | Trent et al. |
| 2008/0015370 A1 | 1/2008 | Hook et al. |

FOREIGN PATENT DOCUMENTS

| GB | 2173496 | 10/1986 |
| GB | 2173496 A | 10/1986 |
| JP | 1994-025196 B2 | 10/1991 |
| JP | 6025196 A | 2/1994 |
| RO | 72086 A2 | 11/1981 |
| RO | 108962 B1 | 10/1994 |

OTHER PUBLICATIONS

Huang et al., AIChE Journal, 52(7), 2518-2534, Apr. 26, 2006.*
Fan, William W. et al, Process for Producing Epoxides, Provisional U.S. Appl. No. 12/512,227, filed Jul. 30, 2009, Dow Internal Reference No. 67143-US-NP[1].
Fan, William W. et al, Process for Producing Epoxides, Provisional U.S. Appl. No. 12/508,435, filed Jul. 23, 2009, Dow Internal Reference No. 67144-US-NP.
Defta, P. et al, Production of Epichlorohydrin—From Propylene Di:Chlorohydrin(s) in Solution and Calcium Hydroxide Suspension, Romanian Patent No. RO108962, Oct. 31, 1994, Derwent World Patent Database (English Abstract).
Niculescu, George et al, Apparatus and Methods for Producing Epichlorohydrin, Romanian Patent No. RO72086, Nov. 24, 1981, Chemical Abstracts Database (English Abstract).
English Patent Abstract of GB 2173496 from esp@cenet, published Oct. 15, 1986, 1 page.
English Patent Abstract of JP 06-025196 from Patent Abstracts of Japan, published Jan. 2, 1994, 2 pages.

\* cited by examiner

*Primary Examiner* — Taylor Victor Oh

(57) ABSTRACT

A process for producing epoxides, the process including: (a) feeding at least one aqueous alkali and at least one halohydrin to a reactive distillation column, wherein the reactive distillation column includes a feed zone, a top zone disposed above the feed zone, and a bottom zone disposed below the feed zone; (b) concurrently in the reactive distillation column: (i) reacting at least a portion of the halohydrin with the alkali to form an epoxide; and (ii) stripping water and the epoxide from a basic aqueous residue; (c) recovering the water and the epoxide from the reactive distillation column as an overheads fraction; (d) condensing and phase separating the overheads fraction to form an organic overheads fraction including the epoxide and an aqueous overheads fraction including water; and (e) maintaining a liquid holdup per plate in the feed zone at a residence time of 10 seconds or less.

18 Claims, 2 Drawing Sheets

PROCESS FOR PRODUCING EPOXIDES

CROSS-REFERENCE TO RELATED APPLICATION

This application, pursuant to 35 U.S.C. §119(e), claims priority to U.S. Provisional Application Ser. No. 61/085,758, filed Aug. 1, 2008, which is hereby incorporated by reference in its entirety.

FIELD OF THE DISCLOSURE

Embodiments disclosed herein relate generally to processes and apparatus to produce epoxides, particularly to processes and apparatus for forming epoxides via halohydrins. More specifically, embodiments disclosed herein relate to dehydrohalogenation processes and apparatus for the continuous production of epoxides by the reaction of halohydrins with alkali, where the epoxides are recovered by distillation.

BACKGROUND

Epoxides, including propylene oxide, butylene oxide, epichlorohydrin, and the like, are widely used precursors for the production of other compounds. Most epoxides are formed via the halohydrin intermediates and these processes are well known to those skilled in the art, as disclosed in U.S. Pat. No. 5,532,389 and British Patent No. 2,173,496. The halohydrins are most often reacted with an aqueous alkali stream to produce the epoxides and the subsequent halide salt. The epoxide-water azeotrope is advantageously stripped from the aqueous stream to minimize by-product losses from the reaction of water with the epoxide to form glycols, such as ethylene glycol, propylene glycol, 3-chloro-1,2-propandiol, glycidol, and glycerine. This overhead product comprising water and epoxide is then condensed and separated in a liquid-liquid phase separator to form an aqueous fraction and an organic fraction containing the crude epoxide, which may be further purified. The aqueous fraction from the overhead is returned to the distillation column as reflux.

In industrial processes, halohydrins are made by reacting low molecular weight olefin-containing compounds, such as propylene, butylene and allyl chloride, with chlorine (or other halogens) and water in a reaction referred to as hypochlorination. The propylene and butylene are converted to chlorohydrins and allyl chloride to dichlorohydrins and subsequently to their respective epoxides (propylene oxide, butylene oxide and epichlorohydrin). This process produces both isomers of the halohydrins and the resulting halohydrins are often dilute in water (<10% by weight) and contain an equivalent of hydrogen chloride (HCl) from the reaction. The halohydrin stream produced by hypochlorination may then be fed directly to a reactive distillation column with an alkali, or first to a pre-reactor for neutralization of the HCl and partial conversion of the halohydrin before introduction into the reactive distillation column. For example, Japanese Patent No. JP 1994-025196(B2 )(JP Publication No. 3223267) discloses a process where dilute dichlorohydrins are mixed with Ca(OH)$_2$ at 40° C. in a pre-reactor and then fed to a 24 plate reactive distillation column where the epoxide (epichlorohydrin) is stripped overhead with water and phase separated from the water in the overhead phase separator to obtain epichlorohydrin in good yields.

Another technology used to a lesser extent in industry is the reaction of glycols with HCl with carboxylic acid catalysis to produce the halohydrins, such as for the production of dichlorohydrins from glycerine as disclosed in U.S. Patent Application No. 20080015370. In this case, mostly one isomer of the halohydrin (1,3-dichlorohydrin) is produced and the remainder of the stream contains less than 30% by weight water and less than 10% HCl by weight. This halohydrin stream is fed with a 10% NaOH stream to a 30 tray reactive distillation column where epichlorohydrin is stripped overhead with water and phase separated from the water in the overhead phase separator to obtain epichlorohydrin in good epichlorohydrin quality.

A third technology used to a lesser extent in industry, specifically for the production of the epoxide, epichlorohydrin, is the catalytic acetoxylation of the propylene into allyl acetate, hydrolysis of the allyl acetate into allyl alcohol, catalytic chlorination of the allyl alcohol into dichlorohydrins as disclosed in U.S. Pat. No. 4,634,784. In this case, mostly one isomer of the halohydrin (2,3-Dichlorohydrin) is produced and the remainder of the stream contains less than 20% by weight water and 5% by weight of HCl. This halohydrin stream is fed with a 9.5% Ca(OH)$_2$ slurry to a column with 10 plates where epichlorohydrin is stripped overhead with water and phase separated from the water in the overhead phase separator to obtain epichlorohydrin in good selectivity.

Epoxides may be produced by the dehydrohalogenation of halohydrins with a base. The halohydrin can be a dilute in aqueous or mostly organic stream and often consists of two isomers as well as HCl. The base is typically an aqueous stream or slurry consisting of NaOH or Ca(OH)$_2$ with or without the presence of a salt, such as NaCl and CaCl$_2$. In order to avoid yield losses of the epoxide to hydrolysis, the epoxide is often stripped during the reaction in a distillation column and pH is maintained as close to neutral as possible, as the hydrolysis rate is catalyzed by both acid and base. The glycols produced with some residual organics are not strippable and are lost in the aqueous stream with the salt formed, which exits the bottom of the distillation column and constitute the major yield loss from the dehydrohalogenation process. The bottom aqueous stream may be treated before discharge or recycle. Thus, hydrolysis losses not only impact epoxide yield but also wastewater treatment cost and capital investment.

A wide variety of processes and apparatus for the dehydrohalogenation of halohydrins have been proposed in the prior art. Romanian Patents Nos. 72086 and 108962 disclose a process for production of epichlorohydrin by reacting dichlorohydrins with Ca(OH)$_2$ in a column reactor with residence times from 0.15 to 0.35 minutes to obtain high selectivity, but with low conversion. In addition, the column residence time profile is not optimized, leading to additional hydrolysis losses.

Accordingly, there exists a need for processes and apparatus for the dehydrohalogenation of halohydrins in which the overall by-product hydrolysis reaction may be reduced in order to obtain good epoxide selectivity and conversion.

SUMMARY OF THE DISCLOSURE

In one aspect, embodiments disclosed herein relate to a process for producing epoxides, the process including: (a) feeding at least one aqueous alkali and at least one halohydrin to a reactive distillation column, wherein the reactive distillation column includes a feed zone, a top zone disposed above the feed zone, and a bottom zone disposed below the feed zone; (b) concurrently in the reactive distillation column: (i) reacting at least a portion of the halohydrin with the alkali to form an epoxide; and (ii) stripping water and the epoxide from a basic aqueous residue; (c) recovering the water and the epoxide from the reactive distillation column as an overheads fraction; (d) condensing and phase separating the overheads fraction to form an organic overheads fraction including the epoxide and an aqueous overheads fraction including water; and, (e) maintaining a liquid holdup per plate in the feed zone at a residence time of 10 seconds or less.

In another aspect, embodiments disclosed herein relate to a process for producing epichlorohydrin, the process including: (a) feeding at least one aqueous alkali and at least one dichlorohydrin to a reactive distillation column, wherein the reactive distillation column includes a feed zone, a top zone disposed above the feed zone, and a bottom zone disposed below the feed zone; (b) concurrently in the reactive distillation column: (i) reacting at least a portion of the dichlorohydrin with the alkali to form epichlorohydrin; and (ii) stripping water and the epichlorohydrin from a basic aqueous residue; (c) recovering the water and the epichlorohydrin from the reactive distillation column as an overheads fraction; (d) condensing and phase separating the overheads fraction to form an organic overheads fraction including the epichlorohydrin and an aqueous overheads fraction including water; and, (e) maintaining a liquid holdup per plate in the feed zone at a residence time of 10 seconds or less.

Other aspects and advantages will be apparent from the following description and the appended claims.

DETAILED DESCRIPTION

In one aspect, embodiments disclosed herein relate generally to processes and apparatus to produce epoxides, particularly to processes and apparatus for forming epoxides via halohydrins. In a more specific aspect, embodiments disclosed herein relate to dehydrohalogenation processes and apparatus for the continuous production of epoxides by the reaction of halohydrins with alkali, where the epoxide is distilled from the alkali reaction mixture.

As used herein, the term "epoxide" refers to a compound containing oxygen attached to separate saturated carbon atoms, preferably on adjacent carbon atoms. Epoxides, also known as oxiranes, are cyclic ethers and may contain from 2 to about 10 carbon atoms and may be linear, branched, or cyclic. The epoxide may be unsubstituted, but may also be inertly substituted. By "inertly substituted" it is meant that the epoxide is substituted with any group which does not undesirably interfere with formation of the halohydrin or the epoxide. Inert substituents include chlorine, bromine, fluorine, phenyl, and the like. Examples of epoxides may include ethylene oxide, propylene oxide, epichlorohydrin, and butylene oxide, among others.

As used herein, the term "halohydrin" refers to a compound containing at least one hydroxyl group and at least one halogen atom attached to separate saturated carbon atoms, such as adjacent carbon atoms. Halohydrins may contain from 2 to about 10 carbon atoms and may be linear, branched, or cyclic. Halohydrins may be unsubstituted, but may also be inertly substituted. By "inertly substituted" it is meant that the halohydrin is substituted with any group which does not undesirably interfere with formation of the halohydrin or the epoxide. Inert substituents include chlorine, bromine, fluorine, phenyl, and the like. Examples of halohydrins may include bromohydrins and chlorohydrins, such as, but not limited to, 1-chloro-2-ethanol; 1-chloro-2-propanol; 2-chloro-1-propanol; 1,3-dichloro-2-propanol; 2,3-dichloro-1-propanol; 1-chloro-2-butanol; and 2-chloro-1-butanol.

As used herein, the terms "by-product" and "hydrolysis product" refer to a compound produced by the hydrolysis of the epoxide, including derivative compounds from the hydrolyzed compounds. Examples include ethylene glycol, propylene glycol, 3-chloro-1,2-propandiol, glycidol, glycerin, butylenes glycol, and their corresponding ethers.

Figure 1:
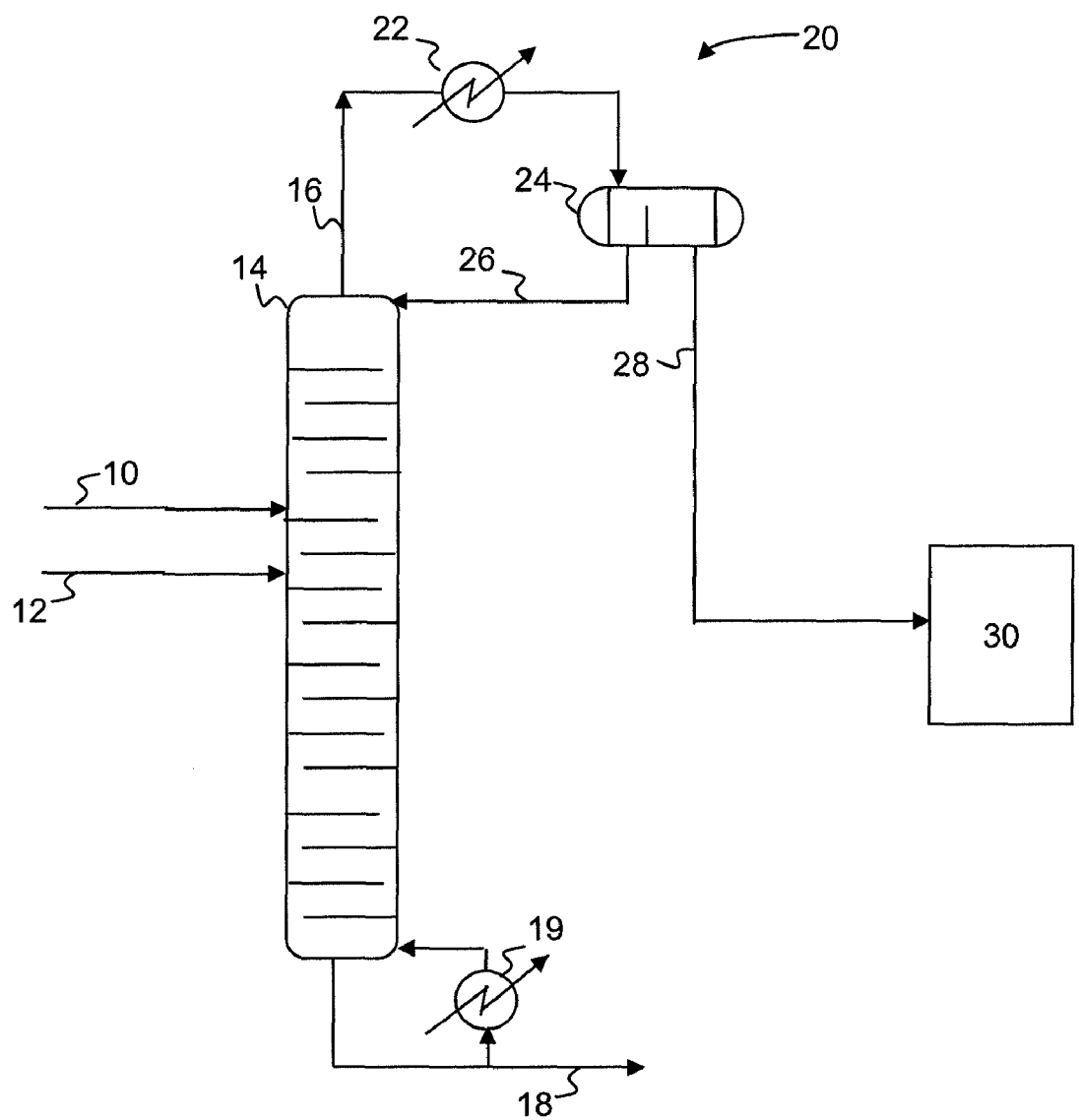
FIG. 1 is a simplified process flow diagram of a process for producing epoxides according to embodiments disclosed herein.

Epoxides may be produced by the dehydrohalogenation of halohydrin with a base, one embodiment of which is illustrated in FIG. 1. At least one aqueous alkali or slurry stream (10) and at least one feed stream comprising halohydrin (12) may be fed to a reactive distillation column (14) to concurrently a) react at least a portion of the halohydrin with the alkali to form an epoxide and b) fractionate water and the epoxide from the basic aqueous residue. The aqueous alkali stream (10) and the halohydrin stream (12) may be fed on different stages or on the same stage. In some embodiments, the aqueous alkali stream (10) is fed above or on the same stage as the halohydrin stream (12). The reactive distillation column (14) may include a plate column, such as a perforated-plate column, a tray column, a bubble-cap plate column and/or a packed column.

The water and epoxide distilled from the reactive distillation column (14) may be recovered as an overheads vapor fraction (16). The basic aqueous residue, including the halide salt, residual epoxide and halohydrin, and hydrolysis reaction by-products, may be recovered from the reactive distillation column (14) as a bottoms fraction (18). A heating or evaporating device (19), such as a reboiler, may be used for heating or evaporating the liquid in the bottom of the reactive distillation column (14) to provide the vapor driving the separation in the column; alternatively, a stripping agent, such as steam, may be introduced into the bottom of the reactive distillation column (14).

The overheads vapor fraction (16) may be condensed and phase separated in overheads system (20), which may include a condenser (22) and a liquid-liquid phase separator (24), to form an organic overheads fraction including the epoxide and an aqueous overheads fraction including water. The condenser (22) may contain at least one heat exchanger and may either partially or completely condense or sub-cool the overhead vapor fraction (16). The condenser (22) may be located above the liquid-liquid phase separator (24) so that the condensed liquid phase flows into the liquid-liquid phase separator (24) via gravity flow. The liquid-liquid phase separator (24) may be a device capable of separating fluids according to their relative density such as a decanter, for example.

At least a portion of the aqueous overheads fraction may be returned to the reactive distillation column (14) as reflux via flow line (26). In other embodiments, at least a portion of the aqueous overheads fraction may be treated by another device such as distillation, membrane filtration, and/or adsorption, to remove the epoxide before being returned to the reactive distillation column (14) as reflux via flow line (26). The organic overheads fraction, a crude epoxide product stream, may be fed via flow line (28) to an epoxide purification system (30) to purify and recover an epoxide product. At least a portion of the bottom fraction (18) may be biologically or chemically treated or treated using a device, such as distillation, evaporation, membrane filtration and/or adsorption, to remove the residual organics for disposal or recycle to chloralkali, lime slaking or hypochlorination processes.

Figure 2:
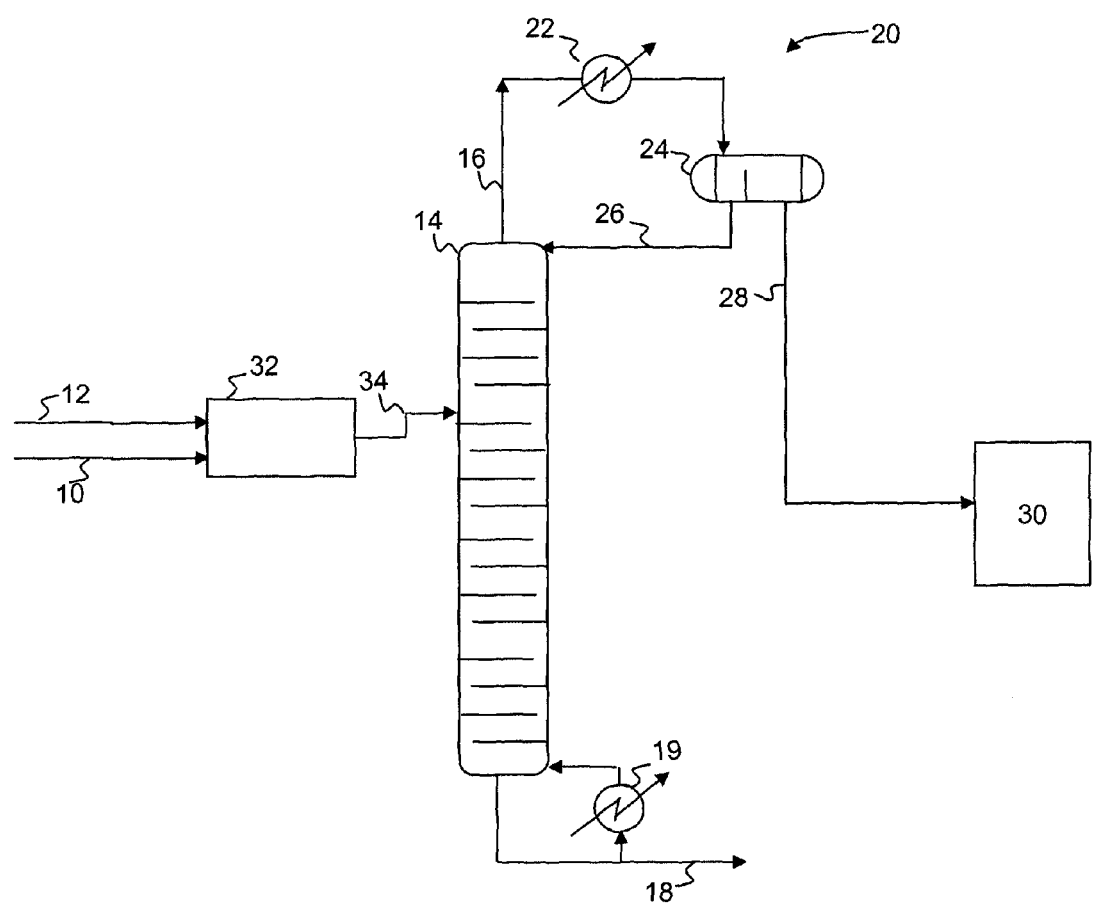
FIG. 2 is a simplified process flow diagram of a process for producing epoxides according to embodiments disclosed herein.

In some embodiments, such as illustrated in FIG. 2, where like numerals represent like parts, at least one feed stream comprising halohydrin (12) may be contacted with at least one aqueous stream comprising alkali (10) in a reactor (32) to convert at least a portion of the halohydrin to epoxide prior to feeding the hydrocarbon and aqueous base to the reactive distillation column (14) via flow line (34). In some embodiments, the reactor (32) may include a continuous stirred tank reactor (CSTR), a plug flow reactor (PFR), a plug flow mixer/reactor, or any other reactor or combinations useful for the conversion of halohydrins to epoxides.

It has been found that the formation of hydrolysis reaction by-products may be different depending on location in the reactive distillation column and the column may be separated into three distinct reaction zones: a) top zone, comprising the plates of the rectification area if one exists; b) feed zone, comprising the plates immediate below the feed point(s); and c) bottom zone, comprising the plates in the bottom part of the column. The top zone has much lower liquid flow than the other two zones and is essential neutral in pH, and thus has a low hydrolysis reaction rate. The feed zone is the most critical with the majority of the dehydrohalogenation reaction occurring and has a high pH level and thus a high hydrolysis reaction rate. The bottom zone has mostly no impact on organic compounds exiting with the wastewater from the bottom of the column and is used to intentionally convert residual unreacted halohydrin and epoxide to glycol for easier wastewater treatment. The same plate design being used for all zones may lead to excess liquid holdup in the top zone and/or insufficient liquid holdup in the bottom zone. In addition, the use of plates with large non-active areas on the plate should be avoided in the top and feed zone to improve the stripping efficiency on the plate for the epoxide.

It has been found that the formation of hydrolysis reaction by-products may be decreased in the reactive distillation column, and thus obtaining high conversion and high selectivity, by maintaining the liquid holdup per plate for the feed zone at a residence time of 10 seconds or less; at a residence time of 7.5 seconds or less in other embodiments; and at a residence time of 5 seconds or less in yet other embodiments. In some embodiments, the feed zone of the distillation column, including the plates immediately below the halohydrin feed point, may include 12 plates or less; 10 plates or less in other embodiments; and 8 plates or less in yet other embodiments. The feed zone plates may be any commercially available plate designed to obtain a low liquid holdup such as valve plate, sieve plate, bubble cap tray, perforated plates, packing and the like. In some embodiments, plates with no downcomers, such as dual flow plates and packing may be used.

It has also been found that the formation of hydrolysis reaction by-products may be decreased in the reactive distillation column by maintaining the liquid holdup per plate for the top zone at a residence time of 20 seconds or less; at a residence time of 10 seconds or less in other embodiments; and at a residence time of 5 seconds or less in yet other embodiments. In some embodiments, the top zone of the distillation column or the rectification section including the plates immediately above the halohydrin feed point, may include 10 plates or less; 8 plates or less in other embodiments; and 6 plates or less in yet other embodiments. The feed zone plates may be any commercially available plate designed to obtain a low liquid holdup such as valve plate, sieve plate, bubble cap tray, perforated plates, packing and the like. In some embodiments, plates with no downcomers, such as dual flow plates and packing may be used.

It has also been found that below the feed zone, there exists a mass transfer limit to stripping the unreacted halohydrin and/or the epoxide from the reaction mixture. This bottom zone may be used to convert these unreacted halohydrins and epoxides to glycols to enable easier treatment of the organics exiting the bottom of the column in the wastewater. The liquid holdup per plate for the bottom zone may be maintained at a residence time of 20 seconds or greater; at a residence time of 10 seconds or greater in other embodiments; and at a residence time of 5 seconds or greater in yet other embodiments. In some embodiments, the bottom zone of the distillation column, including the plates immediately below the feed zone, may include 20 plates or less; 16 plates or less in other embodiments; and 14 plates or less in yet other embodiments. The bottom zone plates may be any commercially available plate designed to obtain the proper liquid holdup, such as valve plate, sieve plate, bubble cap tray, perforated plates, packing and the like.

In some embodiments, the liquid holdup per plate may be attained by adjusting reflux rates and reboil rates. In other embodiments, the liquid holdup per plate may be attained by disposing properly designed trays and/or packing within the reactive distillation column according to standard engineering practice. The plates in the three zones in the reactive distillation column may be trays and/or packing or a combination of the two. Plates with no downcomers and thus no "non-active" areas and packing are preferred for the top and feed zones.

The dehydrohalogenation reaction temperature is not particularly limited; and may be at least 10° C. in some embodiments; at least 30° C. in other embodiments; at least 60° C. in other embodiments; up to 110° C. in other embodiments; up to 100° C. in other embodiments; and up to 90° C. in yet other embodiments. The reaction pressure is not particularly limited, and may range from about 10 millibar to about 1000 millibar. The dehydrohalogenation reaction may be conducted at pressures from about 50 to about 800 millibar in some embodiments; from about 100 to about 500 millibar in other embodiments; and from about 150 to about 400 millibar in yet other embodiments.

In some embodiments, the halohydrin feed stream may include both isomers of the halohydrin. For example, in certain embodiments, the halohydrin feed may include from 0 to 10 percent of the mixture of halohydrins, hydrochloric acid (HCl) in an amount ranging from 0 to about 5 weight percent, and up to about 95 weight percent water. The total halohydrin feed stream may be aqueous and single phase.

In other embodiments, the halohydrin feed stream may include predominately one isomer of the halohydrin. For example, in certain embodiments, the halohydrin feed may include from 55 to 100 percent of the halohydrin, hydrochloric acid (HCl) in an amount ranging from 0 to about 10 weight percent, and up to about 30 weight percent water. The total halohydrin feed may be organic and single phase; or biphasic.

The base may include an aqueous alkali metal hydroxide, such as sodium hydroxide, potassium hydroxide, calcium hydroxide, or mixtures thereof. In some embodiments, the aqueous phase may also include an alkali metal salt, such as a sodium halide salt or a calcium halide salt or the like. The amount and concentration of aqueous alkali metal hydroxide is suitably any which results in formation of the corresponding epoxide. The amount of the inorganic base used is not particularly limited. In some embodiments, the amount of the inorganic base used may range from 1.0 to 1.5 times stoichiometric based on moles of halohydrin and any neutralizable chlorinating agent that may be present such as HCl. In other embodiments, the amount of inorganic base used may range from 1.01 to 1.3 times stoichiometric; and from 1.02 to 1.1 times stoichiometric in other embodiments. High concentration of aqueous alkali metal hydroxide may reduce the water loading into the system and the wastewater produced. A concentration of at least about 1% by weight aqueous alkali metal hydroxide may be used in some embodiments; at least about 5% by weight in other embodiments; at least about 10% by weight in other embodiments; and at a concentration within the range from about 10 to about 35% by weight in yet other embodiments.

Dehydrohalogenation according to embodiments disclosed herein may result in a high selectivity to the epoxide, even at high halohydrin conversions. For example, in some embodiments, the dehydrohalogenation may result in a halohydrin conversion of at least 97 mole percent and a selectivity to the epoxide of at least 97 percent; a selectivity of at least 98 percent in other embodiments. In other embodiments, the dehydrohalogenation may result in a halohydrin conversion of at least 98 mole percent and a selectivity to the epoxide of at least 98 percent; and a conversion of at least 99 mole percent at a selectivity of at least 98 percent in yet other embodiments.

EXAMPLES

In the examples below, a dehydrohalogenation process according to the present invention is simulated based on data collected from prototyping experiments. A dichloropropanol feed (72% 1,3-dichloropropanol, 3% 2,3-dichloropropanol, 5% hydrochloric acid, and 20% water, by weight) is reacted with a 20% sodium hydroxide aqueous solution in a pipe mixer which provides 4 seconds of residence time. The effluent from the pipe mixer is fed to a distillation column operating at an overhead pressure of 300 millibar. The distillation column consists of 2 plates on the top zone, 2 plates on the feed zone and 6 plates on the bottom zone. The liquid holdup (average residence time) per plate is set accordingly to the experiment, as detailed in Table 1. The overhead system consists of a condenser with a decanter set at 40° C. to phase separate the organic and aqueous phases. The aqueous phase is refluxed back to the top tray of the column. The feed to the column enters on the $3^{rd}$ plate from the top. The column is operated at an aqueous reflux to dichloropropanol feed mass ratio of 1.2. Conversion is calculated as 1 minus the ratio of the dichloropropanols in the organic stream from the decanter and the dichloropropanol feed. Yield loss is calculated as the parts per million total organic carbons (TOC) leaving the bottom of the distillation column in the wastewater stream. Results are presented in Table 1.

TABLE 1

| Experiment | Top Zone Time, sec | Feed Zone Time, sec | Bottom Zone Time, sec | Conversion | TOC ppm |
|---|---|---|---|---|---|
| 1 | 115 | 40 | 19 | 99% | 1142 |
| 2 | 115 | 40 | 24 | 99% | 1147 |
| 3 | 29 | 10 | 24 | 99% | 614 |
| 4 | 5 | 5 | 24 | 99% | 476 |
| 5 | 14 | 5 | 24 | 99% | 501 |
| 6 | 24 | 5 | 24 | 99% | 526 |
| 7 | 5 | 15 | 24 | 99% | 621 |
| 8 | 5 | 25 | 24 | 99% | 742 |

As shown by the results in table 1, the liquid holdup in the top zone and the feed zone may each impact product yield, where higher residence times in the feed and top zones may result in additional hydrolysis (higher TOC content). Based on the data presented, the feed zone residence time has a greater impact than tope zone residence time. The liquid holdup in the bottom zone has a low impact on the TOC of the system. The extra residence time does help in converting the epoxide to glycol as in the Example above where the epichlorohydrin is converted to glycerin, which allows for easier wastewater treatment.

As described above, embodiments disclosed herein may provide for reaction of halohydrins with a base to form epoxides at a high selectivity, such as greater than 97%, and a high yield, such as greater than 97%. For example, embodiments disclosed herein may advantageously provide for decreased epoxide hydrolysis in a reactive distillation column used for the conversion of the halohydrin to epoxide. The decreased hydrolysis may be attained by maintaining the liquid holdup per plate in the top zone at 20 seconds or less; in the feed zone at 10 seconds or less; and in the bottom zone at 10 seconds or greater.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for producing epoxides, the process comprising:
   (a) feeding at least one aqueous alkali and at least one halohydrin to a reactive distillation column, wherein the reactive distillation column comprises three distinct reaction zones comprising (i) a feed zone, (ii) a top zone disposed above the feed zone, and (iii) a bottom zone disposed below the feed zone, wherein each of the feed, top, and bottoms zones comprise at least one plate for mass transfer;
   (b) concurrently in the reactive distillation column:
      (i) reacting at least a portion of the halohydrin with the alkali to form an epoxide; and
      (ii) stripping water and the epoxide from a basic aqueous residue;
   (c) recovering the water and the epoxide from the reactive distillation column as an overheads fraction;
   (d) condensing and phase separating the overheads fraction to form an organic overheads fraction comprising the epoxide and an aqueous overheads fraction comprising water;
   (e) maintaining a liquid holdup per plate in the feed zone at a residence time of 10 seconds or less;
   (f) maintaining a liquid holdup per plate in the top zone at a residence time of 20 seconds or less; and
   (g) maintaining a liquid holdup per plate in the bottom zone at a residence time of 10 seconds or greater.

2. The process of claim 1, wherein a liquid holdup per plate in the feed and top zones is maintained at a residence time of 5 seconds or less, and wherein a liquid holdup per plate in the bottom zone is maintained at a residence time of greater than 10 seconds.

3. The process of claim 1, wherein the feed zone comprises 12 plates or less immediately below a location of the halohydrin feed;
   and wherein the top zone comprises 10 plates or less immediately above a location of the halohydrin feed.

4. The process of claim 1, wherein the plates in the top and feed zones are trays with no downcomers, and wherein the trays with no downcomers comprise at least one of dual flow trays and packing.

5. The process of claim 1, further comprising at least one of (i) feeding at least a portion of the aqueous overheads fraction to the reactive distillation column as reflux; (ii) feeding at least a portion of the organic overheads fraction to an epoxide purification system; and (iii) contacting the halohydrin and the aqueous alkali in a reactor to convert at least a portion of the halohydrin to epoxide prior to the feeding.

6. The process of claim 1, wherein the halohydrin comprises at least one of 1-chloro-2-ethanol; 1-chloro-2-propanol; 2-chloro-1-propanol; 1,3-dichloro-2-propanol; 2,3-dichloro-1-propanol; 1-chloro-2-butanol; and 2-chloro-1-butanol.

7. The process of claim 1, wherein the aqueous alkali comprises at least one of sodium hydroxide and calcium hydroxide.

8. The process of claim 7, wherein the aqueous alkali further comprises at least one of a sodium halide salt and a calcium halide salt.

9. The process of claim 1, wherein a halohydrin conversion is at least 98 mole percent, and wherein a selectivity to the epoxide is at least 98 percent.

10. A process for producing epichlorohydrin, the process comprising:
(a) feeding at least one aqueous alkali and at least one dichlorohydrin to a reactive distillation column, wherein the reactive distillation column comprises three distinct reaction zones comprising (i) a feed zone, (ii) a top zone disposed above the feed zone, and (iii) a bottom zone disposed below the feed zone, wherein each of the feed, top, and bottoms zones comprise at least one plate for mass transfer;
(b) concurrently in the reactive distillation column:
(i) reacting at least a portion of the dichlorohydrin with the alkali to form epichlorohydrin; and
(ii) stripping water and the epichlorohydrin from a basic aqueous residue;
(c) recovering the water and the epichlorohydrin from the reactive distillation column as an overheads fraction;
(d) condensing and phase separating the overheads fraction to form an organic overheads fraction comprising the epichlorohydrin and an aqueous overheads fraction comprising water;
(e) maintaining a liquid holdup per plate in the feed zone at a residence time of 10 seconds or less;
(f) maintaining a liquid holdup per plate in the top zone at a residence time of 20 seconds or less; and
(g) maintaining a liquid holdup per plate in the bottom zone at a residence time of 10 seconds or greater.

11. The process of claim 10, wherein a liquid holdup per plate in the feed and top zones is maintained at a residence time of 5 seconds or less, and wherein a liquid holdup per plate in the bottom zone is maintained at a residence time of greater than 10 seconds.

12. The process of claim 10, wherein the feed zone comprises 12 plates or less immediately below a location of the dichlorohydrin feed; and wherein the top zone comprises 10 plates or less immediately above a location of the dichlorohydrin feed.

13. The process of claim 10, wherein the plates in the top and feed zones are trays with no downcomers.

14. The process of claim 13, wherein the trays with no downcomers comprise at least one of dual flow trays and packing.

15. The process of claim 10, further comprising at least one of (i) feeding at least a portion of the aqueous overheads fraction to the reactive distillation column as reflux; (ii) feeding at least a portion of the organic overheads fraction to an epichlorohydrin purification system; and (iii) contacting the dichlorohydrin and the aqueous alkali in a reactor to convert at least a portion of the dichlorohydrin to epichlorohydrin prior to the feeding.

16. The process of claim 10, wherein the aqueous alkali comprises at least one of sodium hydroxide and calcium hydroxide.

17. The process of claim 16, wherein the aqueous alkali further comprises at least one of a sodium halide salt and a calcium halide salt.

18. The process of claim 10, wherein a dichlorohydrin conversion is at least 98 mole percent, and wherein a selectivity to the epichlorohydrin is at least 98 percent.

* * * * *